United States Patent
Strittmatter et al.

(10) Patent No.: US 9,458,401 B2
(45) Date of Patent: *Oct. 4, 2016

(54) USE OF SUBSTITUTED UREAS OR URETHANES FOR IMPROVEMENT OF THE USE PROPERTIES OF MINERAL AND SYNTHETIC NONAQUEOUS INDUSTRIAL FLUIDS

(71) Applicant: BASF SE, Ludwigshafen (DE)

(72) Inventors: Jan Strittmatter, Shanghai (CN); Karl Haeberle, Speyer (DE); Wolfgang Grabarse, Mannheim (DE); Ivette Garcia Castro, Ludwigshafen (DE); Markus Hansch, Speyer (DE); Irene Troetsch-Schaller, Bissersheim (DE); Stephan Schenk, Speyer (DE); Michael Schroers, Bad Duerkheim (DE); Bernhard Lange, Worms (DE)

(73) Assignee: BASF SE, Ludwigshafen (DE)

( * ) Notice: Subject to any disclaimer, the term of this patent is extended or adjusted under 35 U.S.C. 154(b) by 721 days.

This patent is subject to a terminal disclaimer.

(21) Appl. No.: 13/783,708

(22) Filed: Mar. 4, 2013

(65) Prior Publication Data

US 2016/0010020 A1    Jan. 14, 2016

Related U.S. Application Data

(60) Provisional application No. 61/607,619, filed on Mar. 7, 2012.

(51) Int. Cl.

| C10L 10/14 | (2006.01) |
|---|---|
| C10L 1/22 | (2006.01) |
| C10L 10/08 | (2006.01) |
| C07C 275/04 | (2006.01) |
| C10M 133/20 | (2006.01) |
| C10L 1/222 | (2006.01) |

(52) U.S. Cl.
CPC ............. *C10L 10/14* (2013.01); *C07C 275/04* (2013.01); *C10L 1/22* (2013.01); *C10L 10/08* (2013.01); *C10M 133/20* (2013.01); *C10L 1/2227* (2013.01); *C10L 2200/0259* (2013.01); *C10L 2200/0438* (2013.01)

(58) Field of Classification Search
CPC .......... C10L 10/14; C10L 10/08; C10L 1/22; C10L 1/2227; C10L 2200/0259; C10L 2200/0438; C10M 133/20; C07C 275/04
See application file for complete search history.

(56) References Cited

U.S. PATENT DOCUMENTS

| 2,657,984 | A | 11/1953 | Braithwaite, Jr. et al. |
|---|---|---|---|
| 2,710,841 | A * | 6/1955 | Brannen ............... C10M 115/08 508/552 |
| 3,403,013 | A | 9/1968 | Eckert et al. |
| 4,102,797 | A | 7/1978 | Schadenberg |
| 4,491,455 | A | 1/1985 | Ishizaki et al. |
| 2004/0010963 | A1 | 1/2004 | Cross et al. |
| 2004/0224859 | A1* | 11/2004 | Numazawa .......... C10M 115/08 508/364 |
| 2005/0126073 | A1 | 6/2005 | Cross et al. |
| 2011/0258917 | A1 | 10/2011 | Garcia Castro et al. |
| 2011/0271586 | A1 | 11/2011 | Mähling et al. |
| 2011/0315107 | A1 | 12/2011 | Grabarse et al. |
| 2012/0005951 | A1 | 1/2012 | Mähling et al. |
| 2012/0010112 | A1 | 1/2012 | Grabarse et al. |
| 2012/0137573 | A1 | 6/2012 | Völkel et al. |
| 2012/0149617 | A1 | 6/2012 | Lange et al. |
| 2012/0196781 | A1 | 8/2012 | Namiki et al. |
| 2012/0247001 | A1 | 10/2012 | Garcia Castro et al. |

FOREIGN PATENT DOCUMENTS

| EP | 0 061 895 A2 | 10/1982 |
|---|---|---|
| EP | 0 261 957 A2 | 3/1988 |
| EP | 2 489 721 A1 | 8/2012 |
| JP | 56-93796 A | 7/1981 |
| WO | WO 93/18115 A1 | 9/1993 |
| WO | WO 99/29748 A1 | 6/1999 |
| WO | WO 00/44857 A2 | 8/2000 |
| WO | WO 2004/007648 A1 | 1/2004 |
| WO | WO 2004/035715 A1 | 4/2004 |
| WO | WO 2005/054314 A2 | 6/2005 |

OTHER PUBLICATIONS

U.S. Appl. No. 13/953,900, filed Jul. 30, 2013, Walter, et al.
International Search Report issued May 7, 2013 in PCT/EP2012/054008.
U.S. Appl. No. 13/898,766, filed May 21, 2013, Peretolchin, et al.
U.S. Appl. No. 14/767,121, filed Aug. 11, 2015, Adams, et al.
U.S. Appl. No. 13/535,847, filed Jun. 28, 2012, Roeger-Goepfert, et al.
U.S. Appl. No. 13/761,644, filed Feb. 7, 2013, Peretolchin, et al.
U.S. Appl. No. 14/436,951, filed Apr. 20, 2015, Hansch, et al.

* cited by examiner

*Primary Examiner* — Cephia D Toomer
(74) *Attorney, Agent, or Firm* — Oblon, McClelland, Maier & Neustadt, L.L.P

(57) ABSTRACT

The use of substituted diureas, polyureas, bisurethanes or polyurethanes of the formula $R^1X$—CO—$NR^3R^4$ in which X is $R^2N$ or O and $R^1$ to $R^4$ are each independently hydrogen, alkyl radicals, alkenyl radicals, cycloalkyl radicals, aryl radicals or arylalkyl radicals, where at least one variable must be a radical having at least 4 carbon atoms and where the urea or urethane functionality must be replicated via bridging members, for improvement of the use properties of mineral and synthetic nonaqueous industrial fluids.

18 Claims, No Drawings

USE OF SUBSTITUTED UREAS OR URETHANES FOR IMPROVEMENT OF THE USE PROPERTIES OF MINERAL AND SYNTHETIC NONAQUEOUS INDUSTRIAL FLUIDS

The present invention relates to the use of particular substituted ureas or urethanes for improvement of the use properties of mineral and synthetic nonaqueous industrial fluids.

Nonaqueous industrial fluids, which may comprise water components in the individual case but whose essential action is based on nonaqueous components, shall be understood here to mean lubricants, lubricant compositions and lubricant oils in the widest sense, especially motor oils, transmission oils, axle oils, hydraulic fluids, hydraulic oils, compressor fluids, compressor oils, circulation oils, turbine oils, transformer oils, gas motor oils, wind turbine oils, slideway oils, lubricant greases, cooling lubricants, antiwear oils for chains and conveyor systems, metalworking fluids, food-compatible lubricants for industrial processing of foods, and boiler oils for industrial cookers, sterilizers and steam peelers. Use properties which are improved by the substituted ureas or urethanes are especially lubricity, frictional wear, lifetime, corrosion protection, antimicrobial protection, demulsification capacity with regard to easier removal of water and impurities, and filterability.

The present invention further relates to the use of the substituted ureas and urethanes mentioned in fuels and in lubricant formulations, and to such lubricant formulations themselves.

The invention further relates to a mixture which comprises the substituted ureas or urethanes mentioned and organic compounds which improve the cold flow characteristics of mineral oils or crude oils, especially middle distillate fuels, and may already comprise organic compounds suitable for dispersion or for promoting dispersion of paraffin crystals which precipitate under cold conditions out of mineral oils and crude oils, especially middle distillate fuels. The present invention further relates to fuels and fuel additive concentrates which comprise this mixture.

Middle distillate fuels of fossil origin, especially gas oils, diesel oils or light heating oils, which are obtained from mineral oil, have different contents of paraffins depending on the origin of the crude oil. At low temperatures, there is precipitation of solid paraffins at the cloud point ("CP"). In the course of further cooling, the platelet-shaped n-paraffin crystals form a kind of "house of cards structure" and the middle distillate fuel ceases to flow even though its predominant portion is still liquid. The precipitated n-paraffins in the temperature range between cloud point and pour point ("PP") considerably impair the flowability of the middle distillate fuels; the paraffins block filters and cause irregular or completely interrupted fuel supply to the combustion units. Similar disruptions occur in the case of light heating oils.

It has long been known that suitable additives can modify the crystal growth of the n-paraffins in middle distillate fuels. Very effective additives prevent middle distillate fuels from solidifying even at temperatures a few degrees Celsius below the temperature at which the first paraffin crystals crystallize out. Instead, fine, readily crystallizing, separate paraffin crystals are formed, which, even when the temperature is lowered further, pass through filters in motor vehicles and heating systems, or at least form a filtercake which is permeable to the liquid portion of the middle distillates, so that disruption-free operation is ensured. The effectiveness of the flow improvers is typically expressed, in accordance with European standard EN 116, indirectly by measuring the cold filter plugging point ("CFPP"). Cold flow improvers or middle distillate flow improvers ("MDFIs") of this kind which are used include, for example, ethylene-vinyl carboxylate copolymers such as ethylene-vinyl acetate copolymers ("EVA").

One disadvantage of these additives is that the paraffin crystals modified in this way, owing to their higher density compared to the liquid portion, tend to settle out more and more at the bottom of the vessel in the course of storage of the middle distillate fuel. As a result, a homogeneous low-paraffin phase forms in the upper part of the vessel, and a biphasic paraffin-rich layer at the bottom. Since the fuel is usually drawn off just above the vessel bottom both in vehicle fuel tanks and in storage or supply tanks of mineral oil dealers, there is the risk that the high concentration of solid paraffins leads to blockages of filters and metering devices. The further the storage temperature is below the precipitation temperature of the paraffins, the greater this risk becomes, since the amount of paraffin precipitated increases with falling temperature. In particular, fractions of biodiesel also enhance this undesired tendency of the middle distillate fuel to paraffin sedimentation.

By virtue of the additional use of paraffin dispersants or wax antisettling additives ("WASAs"), the problems outlined can be reduced.

In view of declining world mineral oil reserves and the discussion surrounding the environmentally damaging consequences of the consumption of fossil and mineral fuels, interest is rising in the additional use of alternative energy sources based on renewable raw materials. These include in particular native oils and fats of vegetable or animal origin. These are in particular triglycerides of fatty acids having from 10 to 24 carbon atoms, which are converted to lower alkyl esters such as methyl esters. These esters are generally also referred to as "FAMEs" (fatty acid methyl esters).

As is the case for middle distillates of mineral or fossil origin, crystals which can likewise block motor vehicle filters and metering devices precipitate out in the course of cooling of such FAMEs. However, these crystals do not consist of n-paraffins but rather of fatty acid esters; in spite of this, it is possible to characterize fuels based on FAMEs with the same parameters as for the middle distillates of fossil origin (CP, PP, CFPP).

Said mixtures of these FAMEs with middle distillates generally have poorer cold performance than middle distillates of fossil or mineral origin alone. In the case of mixtures with middle distillates of fossil origin, the addition of the FAMEs increases the tendency to form paraffin sediments. In particular, however, the FAMEs mentioned, when they are intended to partly replace middle distillates of fossil origin as biofuel oils, have excessively high CFPP values, such that they cannot be used without difficulty as a fuel or heating oil according to the current country- and region-specific requirements. The increase in the viscosity in the course of cooling also influences the cold properties in FAMEs to a greater extent than in pure middle distillates of fossil or mineral origin.

There have already been proposals of additives which are intended to improve the cold properties of fuels. For instance, U.S. Pat. No. 2,657,984, published Nov. 3, 1953, recommends substituted ureas and substituted urethanes for lowering the pour point in fuel oils. The lowering described therein of the PP values in the fuel oil, however, is only a few ° F. and was determined in the absence of further additives.

Japanese patent application JP-A S56-93796, published Jul. 29, 1981, describes the combination of (A) urea or biuret derivatives of polyisocyanates and relatively long-chain dialkylamines and (B) ethylene-vinyl acetate copolymers as flow improvers for fuel oils. Such flow improvers modify wax crystals in fuel oils in such a way that the flow characteristics of the fuel oil at low temperatures is improved. The radicals on the relatively long-chain dialkylamines mentioned may have 1 to 26 carbon atoms and be linear or branched. Examples of urea or biuret derivatives (A) are the reaction products of di(n-octadecyl)amine or di(dodecyl)amine and toluene diisocyanate, hexamethylene diisocyanate, diphenylmethane 4,4'-diisocyanate, trimethylolpropane/toluene 2,4-diisocyanate (Desmodur® TH) or trimeric hexamethylene diisocyanate (Sumidur® N75).

It was an object of the present invention to provide products which bring about an improvement of the use properties of mineral and synthetic nonaqueous industrial fluids.

In addition, products which bring about improved cold flow characteristics in mineral oils and crude oils were to be provided, especially in middle distillate fuels. More particularly, the CFPP for such fuels was to be lowered in a more effective manner.

The object is achieved in accordance with the invention by the use of (i) substituted ureas or urethanes of the general formula (I)

$$R^1X\text{—}CO\text{—}NR^3R^4 \quad (I)$$

in which the variable X is $R^2N$ or O and the variables $R^1$ to $R^4$ are each independently hydrogen, $C_1$- to $C_{30}$-alkyl radicals which may be interrupted by one or more oxygen atoms, $C_3$- to $C_{30}$-alkenyl radicals, $C_5$- to $C_{30}$-cycloalkyl radicals, $C_6$- to $C_{30}$-aryl radicals or $C_7$- to $C_{30}$-arylalkyl radicals, where at least one of the variables $R^1$ to $R^4$ must be a radical having at least 4 carbon atoms and where one or more of the variables $R^1$ to $R^4$ must be a radical of the formula (Ia)

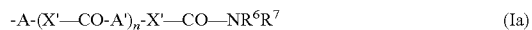

$$\text{-A-}(X'\text{—}CO\text{-}A')_n\text{-}X'\text{—}CO\text{—}NR^6R^7 \quad (Ia)$$

in which the variables A and A' are each an aliphatic, cycloaliphatic, aromatic or aliphatic-aromatic bridging element having 1 to 20 carbon atoms, the variable X' is $NR^5$ or O, the variable n is an integer from 0 to 50 and the variables $R^5$, $R^6$ and $R^7$ are each independently hydrogen, $C_1$- to $C_{30}$-alkyl radicals which may be interrupted by one or more oxygen atoms, $C_3$- to $C_{30}$-alkenyl radicals, $C_5$- to $C_{30}$-cycloalkyl radicals, $C_6$- to $C_{30}$-aryl radicals or $C_7$- to $C_{30}$-arylalkyl radicals, where one or more of the variables $R^5$ to $R^7$ may be a radical having at least 4 carbon atoms, for improvement of the use properties of mineral and synthetic nonaqueous industrial fluids.

The substituted ureas and urethanes of the general formula (I) are diureas ($X=X'=NR^2$) or bisurethanes ($X=X'=O$) in the case that they comprise a radical of the formula (Ia) where n=0, and polyureas ($X=X'=NR^2$) or polyurethanes ($X=X'=O$) in the case that they comprise a radical of the formula (Ia) where n>0. The compounds (I) may also comprise a plurality of, for example two, three or four, radicals of the formula (Ia). It is also possible to use mixed urea/urethane compounds (I) with one or more radicals of the formula (Ia) in which the individual variables X and X' may be either $NR^2$ or O.

Possible $C_1$- to $C_{30}$-alkyl radicals for $R^1$ to $R^7$ are preferably linear or branched alkyl radicals, for example methyl, ethyl, n-propyl, isopropyl, n-butyl, sec-butyl, isobutyl, tert-butyl, pentyl, neopentyl, hexyl, heptyl, octyl, 2-ethylhexyl, neooctyl, nonyl, neononyl, isononyl, decyl, neodecyl, 2-propylheptyl, undecyl, neoundecyl, dodecyl, tridecyl, isotridecyl, tetradecyl, pentadecyl, hexadecyl, heptadecyl, octadecyl (stearyl), nonadecyl, eicosyl, heneicosyl, tricosyl and the constitution isomers thereof.

Alkyl radicals interrupted by one or more oxygen atoms for $R^1$ to $R^7$ having up to 30 carbon atoms are, for example, radicals of the formula —$(CHR^8\text{—}CH_2\text{—}O)_m$—$R^9$ in which the variable $R^8$ is hydrogen, a $C_1$- to $C_4$-alkyl radical such as methyl, ethyl or n-propyl, or phenyl, the variable $R^9$ is as defined for the variables $R^1$ to $R^7$, but especially hydrogen or linear or branched $C_1$- to $C_{20}$-alkyl, and the variable m is an integer from 1 to 30.

Individual examples of such radicals are —$(CH_2\text{—}CH_2\text{—}O)_m$—$R^9$ where m=1 to 15, —$[CH(CH_3)\text{—}CH_2\text{—}O]_m$—$R^9$ where m=1 to 25, —$[CH(C_2H_5)\text{—}CH_2\text{—}O]_m$—$R^9$ where m=1 to 25 and —$(CHPh\text{-}CH_2\text{—}O)_m$—$R^9$ where m=1 to 4, where $R^9$ in each case is hydrogen, methyl, ethyl, 2-ethylhexyl, 2-propylheptyl or isotridecyl.

Possible $C_3$- to $C_{30}$-alkenyl radicals for $R^1$ to $R^7$ are, for example, linear alkenyl radicals such as allyl, oleyl, linolyl and linolenyl.

Relatively long-chain linear alkyl radicals and alkenyl radicals may also be of natural origin and may originate, for example, from mono-, di- and/or triglycerides in oils or fats such as sunflower oil, palm (kernel) oil, soybean oil, rapeseed oil, castor oil, olive oil, peanut oil, coconut oil, mustard oil, linseed oil, cotton seed oil or tallow fat; such alkyl radicals of natural origin are generally mixtures of homologous species or species of similar chain length.

Possible $C_5$- to $C_{30}$-cycloalkyl radicals for $R^1$ to $R^7$ are preferably $C_5$- to $C_{10}$-cycloalkyl radicals, for example cyclopentyl, cyclohexyl, 2-, 3- or 4-methylcyclohexyl, 2,3-, 2,4-, 2,5-, 2,6-, 3,4- or 3,5-dimethylcyclohexyl, cycloheptyl and cyclooctyl.

Possible $C_6$- to $C_{30}$-aryl radicals for $R^1$ to $R^7$ are preferably $C_6$- to $C_{10}$-aryl radicals, for example phenyl, naphthyl, tolyl and o-, m- or p-xylyl.

Possible $C_7$- to $C_{30}$-arylalkyl radicals for $R^1$ to $R^7$ are preferably $C_7$- to $C_{10}$-arylalkyl radicals, for example benzyl, 2-phenylethyl, 3-phenylpropyl and 4-phenylbutyl.

The alkyl, alkenyl, cycloalkyl, aryl and arylalkyl radicals mentioned may comprise, to a small extent, functional groups such as hydroxyl groups or carboxylic ester groups, without destroying the predominant hydrocarbon character of the moiety.

At least one of the variables $R^1$ to $R^4$ and optionally one or more of the variables $R^5$ to $R^7$ has 4 or more, preferably 8 to 30 and in particular 12 to 24 carbon atoms, in order to ensure sufficient oil solubility. The remaining variables $R^1$ to $R^7$ in that case are generally short-chain and are, for example, $C_1$- to $C_4$-alkyl radicals, or are hydrogen.

The variables A and A' denote bridging elements in diureas, bisurethanes, polyureas and polyurethanes. In the case of polyureas and polyurethanes, A and A' may be different or preferably the same. Typical bridging elements A or A' are: polymethylene moieties of the formula —$(CH_2)_p$— where p=1 to 20, especially p=2 to 10, in particular p=3 to 6; $C_5$- to $C_{10}$-cycloalkylene groups such as 1,2-, 1,3- or 1,4-cyclohexylene, the radical of 1,2-, 1,3- or 1,4-dimethylcyclohexane which is bifunctional on the side chains, the bifunctional radical of the isophorone skeleton, or the radical of dicyclohexyl-methane which is bifunctional on the cyclohexane rings; $C_6$- to $C_{10}$-arylene groups such as 1,2-, 1,3- or 1,4-phenylene; $C_5$- to $C_{14}$-alkylarylene moieties such as the aromatic bifunctional radical of diphenylmethane; arylenealkylene moieties having 8 to 14 carbon atoms, such as the aliphatic bifunctional radical of o-, m- or p-xylene.

In a preferred embodiment, use is made of substituted ureas or urethanes of the general formula (I), in which the variable A in the formula (Ia) is 3,5,5-trimethyl-cyclohexan-1-ylene-3-methylene (derived from the isophorone skeleton), 1,6-hexamethylene, 2,4-tolylene, 2,6-tolylene, dicyclohexylmethan-4,4'-ylene or diphenylmethan-4,4'-ylene.

The variable n denotes, in the case of polyureas and polyurethanes, an integer from 1 to 50, preferably 2 to 25, especially 3 to 20 and in particular 4 to 10.

In a preferred embodiment, use is made of substituted ureas or urethanes of the general formula (I), in which the variable X is $R^2N$ where $R^2$ is a radical of the formula (Ia) in which the variable n is 0, the variables $R^1$, $R^3$, $R^5$ and $R^7$ are each hydrogen and the variables $R^4$ and $R^6$ are each the same $C_4$- to $C_{30}$-alkyl radical which may be interrupted by one or more oxygen atoms, $C_4$- to $C_{30}$-alkenyl radical, $C_5$- to $C_{30}$-cycloalkyl radical, $C_6$- to $C_{30}$-aryl radical or $C_7$- to $C_{30}$-arylalkyl radical. The compounds (I) of this embodiment are thus diureas.

Typical examples of usable diureas and bisurethanes of the general formula (I) are the isophorone-derived compounds of the formula (II)

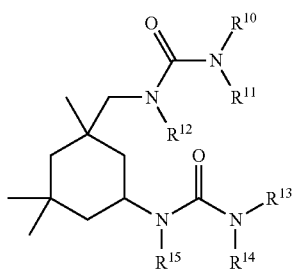

(II)

with the following variable definitions:

| | | |
|---|---|---|
| (IIa) | $R^{12} = R^{15} = H$, | $R^{10} = R^{11} = R^{13} = R^{14} =$ n-butyl, |
| (IIb) | $R^{11} = R^{12} = R^{14} = R^{15} = H$, | $R^{13} = R^{14} =$ 2-ethylhexyl, |
| (IIc) | $R^{11} = R^{12} = R^{14} = R^{15} = H$, | $R^{13} = R^{14} =$ 2-propylheptyl, |
| (IId) | $R^{11} = R^{12} = R^{14} = R^{15} = H$, | $R^{13} = R^{14} =$ n-decyl, |
| (IIe) | $R^{11} = R^{12} = R^{14} = R^{15} = H$, | $R^{13} = R^{14} =$ n-dodecyl, |
| (IIf) | $R^{11} = R^{12} = R^{14} = R^{15} = H$, | $R^{13} = R^{14} =$ n-tridecyl, |
| (IIg) | $R^{11} = R^{12} = R^{14} = R^{15} = H$, | $R^{13} = R^{14} =$ isotridecyl, |
| (IIh) | $R^{11} = R^{12} = R^{14} = R^{15} = H$, | $R^{13} = R^{14} =$ n-tetradecyl, |
| (IIj) | $R^{11} = R^{12} = R^{14} = R^{15} = H$, | $R^{13} = R^{14} =$ n-hexadecyl, |
| (IIk) | $R^{11} = R^{12} = R^{14} = R^{15} = H$, | $R^{13} = R^{14} =$ n-octadecyl, |
| (IIm) | $R^{11} = R^{12} = R^{14} = R^{15} = H$, | $R^{13} = R^{14} =$ oleyl |
| (IIn) | $R^{11} = R^{12} = R^{14} = R^{15} = H$, | $R^{13} = R^{14} =$ phenyl, | and the diureas which are analogous to the compounds (IIa) to (IIn) and have the same $R^{10}$ to $R^{15}$ radicals and have, as bridging element A, a 1,6-hexamethylene, 2,4-tolylene, 2,6-tolylene or diphenylmethan-4,4'-ylene skeleton; and additionally isophorone-derived compounds of the formula (III)

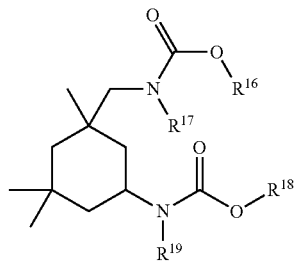

(III)

with the following variable definitions:

| | | |
|---|---|---|
| (IIIa) | $R^{17} = R^{19} = H$, | $R^{16} = R^{18} =$ n-butyl, |
| (IIIb) | $R^{17} = R^{19} = H$, | $R^{16} = R^{18} =$ 2-ethylhexyl, |
| (IIIc) | $R^{17} = R^{19} = H$, | $R^{16} = R^{18} =$ 2-propylheptyl, |
| (IIId) | $R^{17} = R^{19} = H$, | $R^{16} = R^{18} =$ n-decyl, |
| (IIIe) | $R^{17} = R^{19} = H$, | $R^{16} = R^{18} =$ n-dodecyl, |
| (IIIf) | $R^{17} = R^{19} = H$, | $R^{16} = R^{18} =$ n-tridecyl, |
| (IIIg) | $R^{17} = R^{19} = H$, | $R^{16} = R^{18} =$ isotridecyl, |
| (IIIh) | $R^{17} = R^{19} = H$, | $R^{16} = R^{18} =$ n-tetradecyl, |
| (IIIj) | $R^{17} = R^{19} = H$, | $R^{16} = R^{18} =$ n-hexadecyl, |
| (IIIk) | $R^{17} = R^{19} = H$, | $R^{16} = R^{18} =$ n-octadecyl, |
| (IIIm) | $R^{17} = R^{19} = H$, | $R^{16} = R^{18} =$ oleyl, |
| (IIIn) | $R^{17} = R^{19} = H$, | $R^{16} = R^{18} =$ phenyl, | and the bisurethanes which are analogous to the compounds (IIIa) to (IIIn) and have the same $R^{16}$ to $R^{19}$ radicals and have, as bridging element A, a 1,6-hexamethylene, 2,4-tolylene, 2,6-tolylene or diphenylmethan-4,4'-ylene skeleton.

Typical examples of usable polyureas and polyurethanes of the general formula (I) are the reaction product of 1 mol of isophorone diisocyanate with a mixture of 0.5 to 1 mol of tridecylamine and 0.5 to 0.75 mol of isophoronediamine to give a polyurea, and the reaction product of 1 mol of isophorone diisocyanate with a mixture of 0.5 to 1 mol of tridecanol and 0.5 to 0.75 mol of hexane-1,6-diol to give a polyurethane.

The diureas, bisurethanes, polyureas and polyurethane of the general formula (I) are known as such from the prior art and the person skilled in the art is familiar with the options for preparing them. Standard preparation methods for the compounds (I) are based on the reactions of isocyanates with appropriate mono- or polyamines and/or appropriate mono- or polyfunctional alcohols.

Useful isocyanates include the polyisocyanates typically used in polyurethane chemistry, for example aliphatic, aromatic and cycloaliphatic di- and polyisocyanates with hydrocarbyl radicals of corresponding chain length or size and with an NCO functionality of at least 1.8, especially 1.8 to 5 and in particular 2 to 4, and isocyanurates, biurets, allophanates and uretdiones thereof.

Examples of customary diisocyanates are: aliphatic and araliphatic diisocyanates such as tetramethylene diisocyanate, hexamethylene diisocyanate (1,6-diisocyanatohexane), octamethylene diisocyanate, decamethylene diisocyanate, dodecamethylene diisocyanate, tetradecamethylene diisocyanate, esters of lysine diisocyanate, tetramethylxylylene diisocyanate, trimethylhexane diisocyanate or tetramethylhexane diisocyanate; cycloaliphatic diisocyanates such as 1,4-, 1,3- or 1,2-diisocyanatocyclohexane, the trans/trans, cis/cis and cis/trans isomers of 4,4'- or 2,4'-di(isocyanatocyclohexyl)methane, 1-isocyanato-3,3,5-trimethyl-5-(isocyanatomethyl)cyclohexane (isophorone diisocyanate), 2,2- bis(4-isocyanatocyclohexyl)propane, 1,3- or 1,4-bis(isocyanatomethyl)cyclohexane or 2,4- or 2,6-diisocyanato-1-methylcyclohexane; aromatic diisocyanates such as tolylene 2,4- or 2,6-diisocyanate and the isomer mixtures thereof, o-, m- or p-xylylene diisocyanate, 2,4'- or 4,4'-diisocyanatodiphenylmethane and the isomer mixtures thereof, phenylene 1,3- or 1,4-diisocyanate, 1-chlorophenylene 2,4-diisocyanate, naphthylene 1,5-diisocyanate, diphenylene 4,4'-diisocyanate, 4,4'-diisocyanato-3,3'-dimethyldiphenyl, 3-methyldiphenylmethane 4,4'-diisocyanate, 1,4-diisocyanatobenzene or diphenyl ether 4,4'-diisocyanate. It is also possible to use mixtures of the diisocyanates mentioned.

Useful polyisocyanates are also polyisocyanates having isocyanurate groups, uretdione diisocyanates, polyisocyanates having biuret groups, polyisocyanates having urethane or allophanate groups, polyisocyanates comprising oxadiazinetrione groups, uretonimine-modified polyisocyanates of linear or branched $C_4$-$C_{20}$-alkylene diisocyanates, cycloaliphatic diisocyanates having a total of 6 to 20 carbon atoms or aromatic diisocyanates having a total of 8 to 20 carbon atoms, or mixtures thereof.

The usable di- and polyisocyanates preferably have a content of isocyanate groups (calculated as NCO, molecular weight=42 daltons) of 10 to 60% by weight, based on the di- and polyisocyanate (mixture), especially 15 to 60% by weight and in particular 20 to 55% by weight.

Further useful polyisocyanates include:
1. Isocyanurate group-containing polyisocyanates of aromatic, aliphatic, araliphatic and/or cycloaliphatic diisocyanates. Of particular interest here are the corresponding aliphatic and/or cycloaliphatic isocyanato isocyanurates and especially those based on hexamethylene diisocyanate and isophorone diisocyanate. The present isocyanurates are especially tris(isocyanatoalkyl) or tris(isocyanatocycloalkyl) isocyanurates, which are cyclic trimers of the diisocyanates, or mixtures with the higher homologs thereof having more than one isocyanurate ring. The isocyanato isocyanurates generally have an NCO content of 10 to 30% by weight, especially 15 to 25% by weight, and a mean NCO functionality of 3 to 4.5.
2. Uretdione diisocyanates having aromatically, aliphatically, araliphatically and/or cycloaliphatically bonded isocyanate groups, preferably aliphatically and/or cycloaliphatically bonded, and especially those derived from hexamethylene diisocyanate or isophorone diisocyanate. Uretdione diisocyanates are cyclic dimerization products of diisocyanates. The uretdione diisocyanates can be used in the formulations as the sole component or in a mixture with other polyisocyanates, especially those mentioned under 1.
3. Biuret group-containing polyisocyanates with aromatically, cycloaliphatically, aliphatically or araliphatically bonded, preferably cycloaliphatically or aliphatically bonded, isocyanate groups, especially tris(6-isocyanatohexyl)biuret or mixtures thereof with higher homologs thereof. These polyisocyanates having biuret groups generally have an NCO content of 18 to 22% by weight and a mean NCO functionality of 3 to 4.5.
4. Urethane and/or allophanate group-containing polyisocyanates having aromatically, aliphatically, araliphatically or cycloaliphatically bonded, preferably aliphatically or cycloaliphatically bonded, isocyanate groups, as obtainable, for example, by reaction of excess amounts of hexamethylene diisocyanate or of isophorone diisocyanate with polyhydric alcohols, for example trimethylolpropane, neopentyl glycol, pentaerythritol, 1,4-butanediol, 1,6-hexanediol, 1,3-propanediol, ethylene glycol, diethylene glycol, glycerol, 1,2-dihydroxypropane or mixtures thereof. These polyisocyanates having urethane and/or allophanate groups generally have an NCO content of 12 to 20% by weight and a mean NCO functionality of 2.5 to 3.
5. Oxadiazinetrione group-comprising polyisocyanates, preferably derived from hexamethylene diisocyanate or isophorone diisocyanate. Such polyisocyanates comprising oxadiazinetrione groups are preparable from diisocyanate and carbon dioxide.
6. Uretonimine-modified polyisocyanates.

The polyisocyanates mentioned above under points 1. to 6. can be used in a mixture with one another, or else optionally in a mixture with diisocyanates.

Important mixtures of these isocyanates are especially the mixtures of the respective structural isomers of diisocyanatotoluene and diisocyanatodiphenylmethane; a mixture of particular interest is that of 20 mol % of 2,4-diisocyanatotoluene and 80 mol % of 2,6-diisocyanatotoluene. Further particularly advantageous mixtures are those of aromatic isocyanates such as 2,4-diisocyanatotoluene and/or 2,6-diisocyanatotoluene with aliphatic or cycloaliphatic isocyanates such as hexamethylene diisocyanate or isophorone diisocyanate, the preferred mixing ratio of the aliphatic to aromatic isocyanates being 4:1 to 1:4. Also of significance are polycyclic diphenylmethane diisocyanate and uretonimine-containing diphenylmethane diisocyanate (Lupranat® MM 103).

It is also possible to use isocyanates which, as well as the free isocyanate groups, bear further capped isocyanate groups, for example uretdione or urethane groups.

The monoamines which can be reacted with the di- and polyisocyanates mentioned to give urea systems typically bear a primary or secondary amino group. Of particular interest in this context are monoalkylamines and dialkylamines, especially those with at least one relatively long-chain alkyl radical, for example having at least 4, especially at least 8 and in particular at least 12 carbon atoms. Examples of such monoamines are n-butylamine, n-butylmethylamine, n-butylethylamine, n-butyl-n-propylamine, di(n-butyl)amine, n-pentylamine, neopentylamine, n-hexylamine, cyclohexylamine, dicyclohexylamine, n-heptylamine, n-octylamine, di(n-octyl)amine, neooctylamine, 2-ethylhexylamine, di(2-ethylhexyl)amine, n-nonylamine, neononylamine, 2-propyl-heptylamine, di(2-propylheptyl)amine, n-undecylamine, neoundecylamine, n-dodecylamine, n-tridecylamine, isotridecylamine, di(isotridecyl)amine, n-tetradecylamine, n-pentadecylamine, n-hexadecylamine, n-heptadecylamine, n-octadecylamine, oleylamine, linolylamine, linolenylamine, n-nonadecylamine, eicosylamine, heneicosylamine, tricosylamine and the constitutional isomers thereof. The alkyl chains in these amines may also be interrupted by one or more oxygen atoms or by one or more tertiary nitrogen atoms, as in 2-methoxyethylamine, 3-methoxypropylamine, 3-ethoxypropylamine, 3-(2-ethylhexoxy)propylamine, di(2-methoxyethyl)amine, or in analogous or similar relatively long-chain polyetheramines and in 2-(diethylamino)-ethylamine or 2-(diisopropylamino)ethylamine. In addition, it is also possible, for example, to use aromatic and araliphatic amines such as aniline, N-methylaniline, N-ethylaniline, N-(2-hydroxyethyl)aniline, diphenylamine, 2,6-xylidine, o-, m- or p-toluidine, α- or β-naphthylamine, 1-phenylethylamine and 2-phenylethylamine. A further example of a usable primary or secondary monoamine is N-(3-aminopropyl)-imidazole (Lupragen® API).

Di- and polyamines which can be reacted with the di- and polyisocyanates mentioned to give urea systems are generally polyfunctional amines having a molecular weight of 32 to 500 and especially of 60 to 300, which comprise at least two primary or two secondary amino groups or one primary and one secondary amino group. Examples thereof are diamines such as 1,2-diaminoethane, 1,2-diaminopropane, 1,3-diaminopropane, diaminobutanes such as 1,4-diaminobutane, diaminopentanes such as 1,5-diaminopentane or neopentanediamine, diaminohexanes such as 1,6-diaminohexane, diaminooctanes such as 1,8-diaminooctane, piperazine, 2,5-dimethyl-piperazine, amino-3-aminomethyl-3,5,5-trimethylcyclohexane (isophoronediamine), 4,4'-diaminodicyclohexylmethane, 3,3'-dimethyl-4,4'-diaminodicyclohexylmethane, 1,4-diaminocyclohexane, 4,4'-methylenedianiline, aminoethylethanolamine, hydrazine, hydrazine hydrate, or triamines such as diethylenetriamine or 1,8-diamino-4-amino-methyloctane, or higher amines such as triethylenetetramine, tetraethylenepentamine, pentaethylenehexamine, or polymeric amines such as polyethyleneamines, hydrogenated polyacrylonitriles or at least partly hydrolyzed poly-N-vinylformamides, each having a molecular weight of up to 2000 daltons, especially up to 1000 daltons. The alkyl chains in these amines may also be interrupted by one or more oxygen atoms or by one or more tertiary nitrogen atoms, as in 4,7,10-trioxatridecane-1,13-diamine, 4,9-dioxadodecane-1,12-diamine, or in analogous or similar relatively long-chain polyetheramines, for example in aminated ethylene glycol polyethers or glyceryl polyethers, and in N,N-bis(3-aminopropyl)-methylamine.

Examples of alcohols which can be reacted with the di- and polyisocyanates mentioned to give urethane systems are monools, especially alkanols, such as methanol, ethanol, isopropanol, n-propanol, isopropanol, n-butanol, isobutanol, sec-butanol, tert-butanol, n-pentanol, isopentanol, sec-pentanol, tert-pentanol, n-hexanol, n-heptanol, n-octanol, 2-ethylhexanol, n-nonanol, n-decanol, 2-propylheptanol, n-undecanol, n-dodecanol (lauryl alcohol), n-tridecanol, isotridecanol, n-tetradecanol, n-hexadecanol, n-octa-decanol, oleyl alcohol, n-eicosanol, n-heneicosanol, n-tricosanol and ethoxylates and propoxylates of the monools mentioned. Further suitable monools are ethylene glycol monomethyl ether, ethylene glycol monoethyl ether, 1,3-propanediol monomethyl ether, and ethoxylates and propoxylates of long-chain amines and carboxamides, such as coconut fatty amine, oleylamine or oleamide. Further suitable monools are 1-ethynyl-1-cyclohexanol, 2-mercaptoethanol, 2-methyl-3-butyn-2-ol, 3-butyn-2-ol, 4-ethyl-1-octyn-3-ol, ethylenechlorohydrin, propargyl alcohol, dimethylaminoethoxyethanol (Lupragen® N107), dimethylethanolamine (Lupragen® N101) and trimethyl-aminoethylethanolamine (Lupragen® N400). Further suitable monools are derivatives of glycerol and trimethylolpropane in which 2 of the 3 hydroxyl groups have been derivatized, for example glyceryl distearate or glyceryl dioleate.

Further examples of alcohols which can be reacted with the di- and polyisocyanates mentioned to give urethane systems are diols and polyols which may have low molecular weights of typically 50 to 500 daltons, especially 60 to 200 daltons, or high molecular weights of typically 500 to 5000 daltons, especially 1000 to 3000 daltons. Examples of low molecular weight diols of this kind are ethylene glycol, propane-1,2-diol, propane-1,3-diol, butane-1,3-diol, butane-2,3-diol, but-2-ene-1,4-diol, but-2-yne-1,4-diol, pentane-1,2-diol, pentane-1,5-diol, neopentyl glycol, hex-3-yne-2,5-diol, bis(hydroxymethyl)cyclohexanes such as 1,4-bis(hydroxymethyl)cyclohexane, 2-methylpropane-1,3-diol, 2,5-dimethyl-2,5-hexanediol, 2,2'-thiobisethanol, hydroxypivalic acid neopentyl glycol ester, diisopropanol-p-toluidine, N,N-di(2-hydroxyethyl)aniline, diethanolamine, dipropanolamine, diisopropanolamine, and also diethylene glycol, triethylene glycol, tetraethylene glycol, polyethylene glycols, dipropylene glycol, polypropylene glycols, dibutylene glycol and polybutylene glycols. Also suitable are derivatives of triols such as glycerol and trimethylolpropane which are present in monosubstituted form, e.g. glyceryl monooleate. Of particular interest are neopentyl glycol, and alcohols of the general formula HO—$(CH_2)_x$—OH where x is a number from 1 to 20, especially an even number from 2 to 20. Examples thereof are 1,2-ethylene glycol, butane-1,4-diol, hexane-1,6-diol, octane-1,8-diol, decane-1,10-diol and dodecane-1,12-diol.

The low molecular weight diols mentioned are also used as formation components for the preparation of the polyester polyols listed below, preference being given here to the unbranched diols having 2 to 12 carbon atoms and an even number of carbon atoms, and also to pentanediol-1,5 and neopentyl glycol.

Alcohols having a higher functionality than 2, especially having 3 hydroxyl groups, which may serve to establish a certain degree of branching or crosslinking, are, for example, trimethylolbutane, trimethylolpropane, trimethylolethane, pentaerythritol, glycerol, triethanolamine, tripropanolamine, triisopropanolamine, sugar alcohols such as sorbitol, mannitol, diglycerol, threitol, erythritol, adonitol (ribitol), arabitol (lyxitol), xylitol, dulcitol (galactitol), maltitol or isomalt, and also sugars.

Additionally useful here are also monoalcohols which, as well as the hydroxyl group, bear a further group reactive toward isocyanates, especially amino alcohols such as monoalcohols having one or more primary and/or secondary amino groups, for example monoethanolamine, 3-amino-1-propanol, 5-amino-1-pentanol, 3-dimethylaminopropan-1-ol, 1-(2-hydroxyethyl)piperazine, 4-(2-hydroxyethyl)morpholine, 2-(2-aminoethoxy)ethanol, N-methyldiethanolamine, N-butylethanolamine, N,N-dibutylethanolamine, N,N-diethylethanolamine, N,N-dimethylethanolamine, butyldiethanolamine, N-ethylethanolamine, N,N-dimethylisopropanolamine, N-methylethanolamine, diethanolamine, Isopropanolamine, N-(2-hydroxyethyl)aniline and N-(2-aminoethyl)ethanolamine.

Examples of higher molecular weight diols and polyols are firstly polyester polyols. Of particular interest are polyester polyols which are obtained by reaction of the above-mentioned low molecular weight diols with dibasic carboxylic acids. Instead of the free polycarboxylic acids, it is also possible to use the corresponding polycarboxylic anhydrides or corresponding polycarboxylic esters of lower alcohols or mixtures thereof to prepare the polyester polyols. The polycarboxylic acids may be aliphatic, cycloaliphatic, araliphatic, aromatic or heterocyclic, and may optionally be substituted, for example by halogen atoms, and/or unsaturated. Examples of usable dibasic carboxylic acids or derivatives thereof include: suberic acid, azelaic acid, phthalic acid, isophthalic acid, phthalic anhydride, tetrahydrophthalic anhydride, hexahydrophthalic anhydride, tetrachlorophthalic anhydride, endomethylenetetrahydrophthalic anhydride, glutaric anhydride, maleic acid, maleic anhydride, fumaric acid, and also dimeric fatty acids. Preference is given to dicarboxylic acids of the formula HOOC—$(CH_2)_y$—COOH in which y is a number from 1 to 20, especially an even number from 2 to 20, e.g. succinic acid, adipic acid, dodecanedicarboxylic acid and sebacic acid.

Further useful higher molecular weight diols are also polycarbonate diols, as obtainable, for example, by reaction of phosgene with an excess of the low molecular weight diols mentioned as formation components for the polyester polyols.

Suitable higher molecular weight diols are also lactone-based polyester diols, which are homo- or copolymers of lactones, especially terminal hydroxyl group-containing addition products of lactones onto suitable difunctional starter molecules. Useful lactones preferably include those derived from hydroxycarboxylic acids of the general formula HO—$(CH_2)_z$—COOH in which z is a number from 1 to 20, especially an odd number from 3 to 19, for example ε-caprolactone, β-propiolactone, γ-butyrolactone and/or methyl-ε-caprolactone, and mixtures thereof. Suitable starter components are, for example, the low molecular weight diols mentioned above as formation components for the polyesterpolyols. The corresponding polymers of ε-caprolactone are of particular interest. It is also possible to use lower molecular weight polyester diols or polyether diols as starters for preparation of the lactone polymers. Instead of the polymers of lactones, it is also possible to use the corresponding chemically equivalent polycondensates of the hydroxycarboxylic acids corresponding to the lactones.

In addition, useful higher molecular weight diols are also polyether diols. They are obtainable especially by polymerization of ethylene oxide, propylene oxide, butylene oxide, tetrahydrofuran, styrene oxide or epichlorohydrin with themselves, for example in the presence of $BF_3$, or by addition of these compounds, optionally in a mixture or in succession, onto start components with reactive hydrogen atoms such as alcohols or amines, for example water, ethylene glycol, propane-1,2-diol, propane-1,3-diol, 2,2-bis(4-hydroxydiphenyl)propane or aniline. Of particular interest is polytetrahydrofuran having a molecular weight of 250 to 5000, and in particular 1000 to 4500.

The polyester diols and polyether diols mentioned can also be used as mixtures in a ratio of 0.1:1 to 1:9.

The conditions for the reaction of the isocyanates mentioned with the mono- or polyamines mentioned and/or the mono- or polyfunctional alcohols mentioned are likewise familiar to the person skilled in the art. For instance, the polyaddition of the isocyanates onto the amines or alcohols is effected generally at reaction temperatures of 20 to 180° C., especially of 50 to 150° C., and under standard pressure. The reaction times required may extend over a few minutes to a few hours. The person skilled in the art in the field of polyurethane chemistry knows how the reaction time can be influenced by a multitude of parameters such as temperature, concentration of the monomers or reactivity of the monomers.

To accelerate the reaction of the isocyanates, the customary catalysts can be used in addition. Useful catalysts for this purpose in principle include all of those used customarily in polyurethane chemistry. These are, for example, organic amines, especially tertiary aliphatic, cycloaliphatic or aromatic amines, and/or Lewis acidic organic metal compounds. Examples of useful Lewis-acidic organic metal compounds include, for example, tin compounds, for example tin(II) salts of organic carboxylic acids, e.g. tin(II) acetate, tin(II) octoate, tin(II) ethylhexanoate and tin(II) laurate, and the dialkyltin(IV) salts of organic carboxylic acids, e.g. dimethyltin diacetate, dibutyltin diacetate, dibutyltin dibutyrate, dibutyltin bis(2-ethylhexanoate), dibutyltin dilaurate, dibutyltin maleate, dioctyltin dilaurate and dioctyltin diacetate. Metal complexes such as acetylacetonates of iron, titanium, aluminum, zirconium, manganese, nickel and cobalt are also possible, for example zirconium acetylacetonate and zirconium 2,2,6,6-tetramethyl-3,5-heptanedionate. In addition, it is also possible to use bismuth and cobalt catalysts and cesium salts as catalysts, for example cesium carboxylates.

The reaction of the isocyanates mentioned with the mono- or polyamines mentioned and/or the mono- or polyfunctional alcohols mentioned can be performed in the presence or absence of solvents. Examples of suitable solvents are aprotic solvents such as open-chain or cyclic carbonates, lactones, di(cyclo)alkyl dipropylene glycol ethers, N-(cyclo)alkylcaprolactams, N-(cyclo)alkylpyrrolidones, ketones, hydrocarbons and amides.

Useful polymerization apparatuses for the reaction of the isocyanates mentioned with the mono- or polyamines mentioned and/or the mono- or polyfunctional alcohols mentioned include stirred tanks, especially when additional use of solvents ensures a low viscosity and good heat removal. If the reaction is performed in substance, extruders are particularly suitable due to the usually high viscosities and the usually only short reaction times, especially self-cleaning multiscrew extruders.

The substituted ureas and urethanes described are likewise suitable for improvement of the cold flow properties and/or the lubricant properties and/or the conductivity and/or the oxidation insensitivity and/or the dispersion characteristics of mineral oils and crude oils. The corresponding uses therefore also form part of the subject matter of the present invention.

The substituted ureas and urethanes described are preferably suitable for improvement of the cold flow properties and/or of the lubricant properties of fuels, especially of middle distillate fuels. In this context, the substituted ureas and urethanes described are particularly used for dispersion or for promoting dispersion of paraffin crystals which have precipitated out of fuels under cold conditions.

In a particularly preferred embodiment, the substituted ureas and urethanes described are used in the dispersion or for promoting dispersion of paraffin crystals which precipitate out of fuels under cold conditions, in combination with at least one organic compound which improves the cold flow characteristics of middle distillate fuels and is selected from (a1) copolymers of a $C_2$- to $C_{40}$-olefin with at least one further ethylenically unsaturated monomer;
(a2) comb polymers;
(a3) polyoxyalkylenes;
(a4) polar nitrogen compounds;
(a5) sulfocarboxylic acids or sulfonic acids or derivatives thereof; and
(a6) poly(meth)acrylic esters.

It is possible to use either mixtures of different representatives from one of the particular classes (a1) to (a6) or mixtures of representatives from different classes (a1) to (a6).

Preferably, substituted ureas or urethanes of the general formula (I) are used in mineral oils or crude oils which comprise, as a further component, at least one (a1) copolymer of a $C_2$- to $C_{40}$-olefin with at least one further ethylenically unsaturated monomer.

Suitable $C_2$- to $C_{40}$-olefin monomers for the copolymers (a1) are, for example, those having 2 to 20 and especially 2 to 10 carbon atoms, and 1 to 3 and preferably 1 or 2 carbon-carbon double bonds, especially having one carbon-carbon double bond. In the latter case, the carbon-carbon double bond may be arranged either terminally (α-olefins) or internally. However, preference is given to α-olefins, more preferably α-olefins having 2 to 6 carbon atoms, for example propene, 1-butene, 1-pentene, 1-hexene and in particular ethylene.

In the copolymers (a1), the at least one further ethylenically unsaturated monomer is preferably selected from alkenyl carboxylates, (meth)acrylic esters and further olefins. When further olefins are also copolymerized, they are preferably higher in molecular weight than the abovementioned $C_2$- to $C_{40}$-olefin base monomer. When, for example, the olefin base monomer used is ethylene or propene, suitable further olefins are especially $C_{10}$- to $C_{40}$-α-olefins. Further olefins are in most cases only additionally copolymerized when monomers with carboxylic ester functions are also used.

Suitable (meth)acrylic esters are, for example, esters of (meth)acrylic acid with $C_1$- to $C_{20}$-alkanols, especially $C_1$- to $C_{10}$-alkanols, in particular with methanol, ethanol, propanol, isopropanol, n-butanol, sec-butanol, isobutanol, tert-butanol, pentanol, hexanol, heptanol, octanol, 2-ethylhexanol, nonanol and decanol, and structural isomers thereof.

Suitable alkenyl carboxylates are, for example, $C_2$- to $C_{14}$-alkenyl esters, for example the vinyl and propenyl esters, of carboxylic acids having 2 to 21 carbon atoms, whose hydrocarbon radical may be linear or branched. Among these, preference is given to the vinyl esters. Among the carboxylic acids with a branched hydrocarbon radical, preference is given to those whose branch is in the α-position to the carboxyl group, the α-carbon atom more preferably being tertiary, i.e. the carboxylic acid being a so-called neocarboxylic acid. However, the hydrocarbon radical of the carboxylic acid is preferably linear.

Examples of suitable alkenyl carboxylates are vinyl acetate, vinyl propionate, vinyl butyrate, vinyl 2-ethylhexanoate, vinyl neopentanoate, vinyl hexanoate, vinyl neononanoate, vinyl neodecanoate and the corresponding propenyl esters, preference being given to the vinyl esters. A particularly preferred alkenyl carboxylate is vinyl acetate; typical copolymers of group (a1) resulting therefrom are ethylene-vinyl acetate copolymers ("EVAs"). Very particular preference is given to using, as component (a1), at least one such ethylene-vinyl acetate copolymer. Ethylene-vinyl acetate copolymers usable particularly advantageously and their preparation are described in WO 99/29748.

Suitable copolymers (a1) are also those which comprise two or more different alkenyl carboxylates in copolymerized form, which differ in the alkenyl function and/or in the carboxylic acid group. Likewise suitable are copolymers which, as well as the alkenyl carboxylate(s), comprise at least one olefin and/or at least one (meth)acrylic ester in copolymerized form.

In a further preferred embodiment, (a1) is at least one terpolymer of a $C_2$- to $C_{40}$-α-olefin, a $C_1$- to $C_{20}$-alkyl ester of an ethylenically unsaturated monocarboxylic acid having 3 to 15 carbon atoms and a $C_2$- to $C_{14}$-alkenyl ester of a saturated monocarboxylic acid having 2 to 21 carbon atoms. Terpolymers of this kind are described in WO 2005/054314. A typical terpolymer of this kind is formed from ethylene, 2-ethylhexyl acrylate and vinyl acetate.

The or the further ethylenically unsaturated monomer(s) are copolymerized into the copolymers (a1) in an amount of preferably 1 to 50% by weight, especially 10 to 45% by weight and in particular 20 to 40% by weight, based on the overall copolymer. The main proportion in terms of weight of the monomer units in the copolymers (a1) therefore originates generally from the $C_2$ to $C_{40}$ base olefins.

The copolymers (a1) preferably have a number-average molecular weight $M_n$ of 1000 to 20 000 daltons, more preferably 1000 to 10 000 daltons and especially 1000 to 8000 daltons.

As well as the preferred copolymers of class (a1), it is also advantageously possible to use the compounds of classes (a2) to (a6) as components together with the substituted ureas and urethanes described.

Comb polymers suitable as compounds (a2) are, for example, those described in WO 2004/035715 and in "Comb-Like Polymers. Structure and Properties", N. A. Plate and V. P. Shibaev, J. Poly. Sci. Macromolecular Revs. 8, pages 117 to 253 (1974). Further suitable comb polymers (a2) are, for example, those obtainable by the copolymerization of maleic anhydride or fumaric acid with another ethylenically unsaturated monomer, for example with an α-olefin or an unsaturated ester, such as vinyl acetate, and subsequent esterification of the anhydride or acid function with an alcohol having at least 10 carbon atoms. Further preferred comb polymers are copolymers of α-olefins and esterified comonomers, for example esterified copolymers of styrene and maleic anhydride or esterified copolymers of styrene and fumaric acid. Mixtures of comb polymers are also suitable. Comb polymers may also be polyfumarates or polymaleates. Homo- and copolymers of vinyl ethers are also suitable comb polymers.

Polyoxyalkylenes suitable as compounds (a3) are, for example, polyoxyalkylene esters, ethers, ester/ethers and mixtures thereof, especially based on polyethylene glycols or polypropylene glycols. The polyoxyalkylene compounds preferably comprise at least one linear alkyl group, more preferably at least two linear alkyl groups, each having 10 to 30 carbon atoms and a polyoxyalkylene group having a number-average molecular weight of up to 5000 daltons, especially of 100 to 5000 daltons. The alkyl group of the polyoxyalkylene radical comprises preferably 1 to 4 carbon atoms. Also of particular interest here are polyoxyalkylene esters and diesters of fatty acids having 10 to 30 carbon atoms, such as stearic acid or behenic acid. Such polyoxyalkylene compounds are described, for example, in EP-A 061 895 and also in U.S. Pat. No. 4,491,455.

Suitable compounds (a4) are the polar nitrogen compounds described below under component (ii).

Suitable compounds (a5) are sulfocarboxylic acids or sulfonic acids or derivatives thereof, as described, for example, in EP-A-0 261 957. Such sulfocarboxylic acids or sulfonic acids are especially the reaction products of 1 mol of ortho-sulfobenzoic acid or the cyclic anhydride thereof with 2 mol of a long-chain dialkylamine such as hydrogenated ditallowamine.

Poly(meth)acrylic esters suitable as compounds (a6) are either homo- or copolymers of acrylic and methacrylic esters. Preference is given to copolymers of at least two different (meth)acrylic esters which differ with regard to the esterified alcohol. The copolymer optionally comprises another different olefinically unsaturated monomer in copolymerized form. The weight-average molecular weight of the polymer is preferably 50 000 to 500 000 daltons. A particularly preferred polymer is a copolymer of methacrylic acid and methacrylic esters of saturated $C_{14}$ and $C_{15}$ alcohols, the acid groups having been neutralized with hydrogenated tallamine. Suitable poly(meth)acrylic esters are described, for example, in WO 00/44857.

The substituted ureas and urethanes described are additionally suitable for improvement of the cold flow properties and/or of the lubrication properties of mineral and synthetic lubricants and lubricant formulations produced therefrom.

The corresponding uses therefore also form part of the subject matter of the present invention. The present invention likewise provides these lubricant formulations which have been produced from mineral and synthetic lubricants and which comprise at least one of the substituted ureas described or at least one of the substituted urethanes described and at least one further additive component customary for lubricant formulations.

Lubricant formulations shall be understood here to mean especially motor oils, and transmission oils including manual and automatic oils. Motor oils consist typically of mineral base oils which comprise predominantly paraffinic constituents and are produced by complex workup and purification operations in the refinery, with a proportion of normally about 2 to 10% by weight of additives (based on the active substance contents). For specific applications, for example high-temperature uses, the mineral base oils can be replaced partly or fully by synthetic components such as organic esters, synthetic hydrocarbons such as olefin oligomers, poly-$\alpha$-olefins or polyolefins, or hydrocracking oils. Motor oils must also have sufficiently high viscosities at high temperatures to ensure an impeccable lubrication effect and good sealing between cylinder and piston. In addition, the flow properties of motor oils must also be such that the engine can be started without any problem at low temperatures. Motor oils must be oxidation-stable and, even under severe working conditions, must generate only a low level of decomposition products in liquid or solid form and deposits. Motor oils disperse solids (dispersant characteristics), prevent deposits (detergent characteristics), neutralize acidic reaction products and form an antiwear film on the metal surfaces in the engine. Motor oils for internal combustion engines, especially for gasoline engines, Wankel engines, two-stroke engines and diesel engines, are typically characterized by viscosity classes (SAE classes); of particular interest here are fuel-economy motor oils, especially of the SAE 5 W to 20 W viscosity classes to DIN 51511.

Transmission oils including manual and automatic oils are of similar composition to motor oils in terms of their base components and additives. A high proportion of the force is transmitted in the gear system of gearboxes through the liquid pressure in the transmission oil between the teeth. The transmission oil must accordingly be such that it withstands sustained high pressures without decomposing. As well as the viscosity properties, the crucial parameters here are wear, pressure resistance, friction, shear stability, traction and run-in characteristics.

The inventive lubricant formulations comprise the substituted ureas or urethanes described in an amount of typically 0.001 to 20% by weight, preferably 0.01 to 10% by weight, especially 0.05 to 8% by weight and in particular 0.1 to 5% by weight, based on the total amount of the lubricant formulation.

The inventive lubricant formulations may be additized in a customary manner, which means that they comprise, as well as the base oil components typical for the end use thereof, such as mineral or synthetic hydrocarbons, polyethers or esters or mixtures thereof, also customary additives other than dispersants, such as detergent additives (HD additives), antioxidants, viscosity index improvers, pour point depressants (cold flow improvers), extreme pressure additives, friction modifiers, antifoam additives (defoamers), corrosion inhibitors (metal deactivators), emulsifiers, dyes and fluorescent additives, preservatives and/or odor improvers, in the amounts customary therefor. It will be appreciated that the substituted ureas and urethanes described can also be used in the lubricant formulations together with other additives with dispersing action, more particularly with other ashless additives with dispersing action, for example with polyisobutylsuccinic acid derivatives.

The present invention also provides a mixture comprising
(i) 1 to 99% by weight, especially 5 to 95% by weight and in particular 10 to 50% by weight of at least one substituted urea or substituted urethane of the general formula (I)
(ii) 0 to 50% by weight, especially 0 to 40% by weight and in particular 0 to 30% by weight of at least one further organic compound which is different than (i) and is suitable for dispersion or for promoting dispersion of paraffin crystals which precipitate under cold conditions and
(iii) 1 to 99% by weight, especially 5 to 95% by weight and in particular 10 to 50% by weight of at least one organic compound which is different than (i) and (ii) and improves the cold flow characteristics of mineral oils and crude oils, where the sum of all components (i) to (iii) adds up to 100% by weight.

Mineral oils in the context of the present invention are understood to mean the oils produced by distillation from brown coal, hard coal, peat, wood, mineral oil and other mineral or fossil raw materials suitable for this purpose, in refineries and similar production operations. In contrast to fats and fatty oils such as FAME, these mineral oils consist predominantly or exclusively of paraffinic, naphthenic and aromatic hydrocarbons. These oils may additionally also comprise alkenes (olefins), and amounts of sulfur-containing and nitrogen-containing organic compounds which vary according to provenance.

Mineral oils in the context of the present invention are additionally understood to mean all upgraded tradable products produced from these mineral oils by further purification steps such as fractional distillation or catalytic hydrogenation, or by addition of further components or of additives, more particularly fuels, fuel oils, heating oils, lubricants or operating fluids. Of particular interest in this context are fuels such as gasoline fuels (gasoline) and especially middle distillate fuels such as diesel fuels and turbine fuels (jet fuel), and also heating oils.

Crude oils are understood in the context of the present invention to mean mineral oils which have not been treated any further, from which mineral oils are produced by distillation after the production and transport thereof, for example by pipeline or by ship, from the production sites to the refineries.

The inventive mixture is thus suitable as an additive to mineral oils and crude oils, especially to middle distillate fuels, which may also be mixtures of biofuel oils and middle distillate fuels of mineral or fossil origin. Their addition serves principally to improve the cold flow characteristics of these liquids. Middle distillate fuels of mineral or fossil origin, which find use especially as gas oils, petroleum, diesel oils (diesel fuels), turbine fuels, kerosene or (light) heating oils, are often also referred to as fuel oils. Such middle distillate fuels generally have boiling points of 120 to 450° C.

The inventive interaction of components (i), (iii) and optionally (ii) in mineral oils and crude oils improves the cold flow characteristics in the course of transport thereof, for example through pipes, pipelines and lines, and in the course of storage thereof, for example in storage tanks. Further positive effects which are brought about as a result are better handling, for example better filterability.

Component (ii) ensures dispersion or promotes dispersion of paraffin crystals which precipitate out of the mineral oils and crude oils under cold conditions. These are wax antisettling additives (WASAs). In this case, component (ii) enhances the possible dispersing action of component (i), the substituted ureas or urethanes.

In a preferred embodiment, substituted ureas or urethanes of the general formula (I) are used in mineral oils or crude oils which comprise at least one polar nitrogen compound as component (ii).

Polar nitrogen compounds suitable as component (ii) may be either ionic or nonionic and preferably have at least one substituent, especially at least two substituents, in the form of a tertiary nitrogen atom of the general formula $>NR^{23}$ in which $R^{23}$ is a $C_8$-$C_{40}$-hydrocarbyl radical. The nitrogen substituents may also be quaternized, i.e. be in cationic form. An example of such nitrogen compounds is that of ammonium salts and/or amides which are obtainable by the reaction of at least one amine substituted by at least one hydrocarbyl radical with a carboxylic acid having 1 to 4 carboxyl groups or with a suitable derivative thereof. The amines preferably comprise at least one linear $C_8$-$C_{40}$-alkyl radical. Primary amines suitable for preparing the polar nitrogen compounds mentioned are, for example, n-octylamine, n-nonylamine, n-decylamine, n-undecylamine, n-dodecylamine, n-tetradecylamine and the higher linear homologs. Secondary amines suitable for this purpose are, for example, di-n-octadecylamine and methylbehenylamine. Also suitable for this purpose are amine mixtures, in particular amine mixtures obtainable on the industrial scale, such as fatty amines or hydrogenated tallamines, as described, for example, in Ullmann's Encyclopedia of Industrial Chemistry, 6th Edition, "Amines, aliphatic" chapter. Acids suitable for the reaction are, for example, cyclohexane-1,2-dicarboxylic acid, cyclohexene-1,2-dicarboxylic acid, cyclopentane-1,2-dicarboxylic acid, naphthalenedicarboxylic acid, phthalic acid, isophthalic acid, terephthalic acid and succinic acids substituted by long-chain hydrocarbyl radicals.

Further examples of suitable polar nitrogen compounds are ring systems which bear at least two substituents of the formula -A"-$NR^{24}R^{25}$ in which A" is a linear or branched aliphatic hydrocarbyl group optionally interrupted by one or more moieties selected from O, S, $NR^{36}$ and CO, and $R^{24}$ and $R^{25}$ are each a $C_9$- to $C_{40}$-hydrocarbyl radical optionally interrupted by one or more moieties selected from O, S, $NR^{36}$ and CO and/or substituted by one or more substituents selected from OH, SH and $NR^{36}R^{37}$, where $R^{36}$ is $C_1$- to $C_{40}$-alkyl optionally interrupted by one or more moieties selected from CO, $NR^{37}$, O and S and/or substituted by one or more radicals selected from $NR^{38}R^{39}$, $OR^{38}$, $SR^{38}$, $COR^{38}$, $COOR^{38}$, $CONR^{38}R^{39}$, aryl and heterocyclyl, where $R^{38}$ and $R^{39}$ are each independently selected from H and $C_1$- to $C_4$-alkyl and where $R^{37}$ is H or $R^{36}$.

More particularly, component (ii) is an oil-soluble reaction product of poly($C_2$- to $C_{20}$-carboxylic acids) having at least one tertiary amino group with primary or secondary amines. The poly($C_2$- to $C_{20}$-carboxylic acids) which have at least one tertiary amino group and form the basis of this reaction product comprise preferably at least 3 carboxyl groups, especially 3 to 12 and in particular 3 to 5 carboxyl groups. The carboxylic acid units in the polycarboxylic acids have preferably 2 to 10 carbon atoms, and are especially acetic acid units. The carboxylic acid units are suitably bonded to the polycarboxylic acids, for example via one or more carbon and/or nitrogen atoms.

They are preferably attached to tertiary nitrogen atoms which, in the case of a plurality of nitrogen atoms, are bonded via hydrocarbon chains.

Component (ii) is preferably an oil-soluble reaction product based on poly($C_2$- to $C_{20}$-carboxylic acids) which have at least one tertiary amino group and are of the general formula IVa or IVb

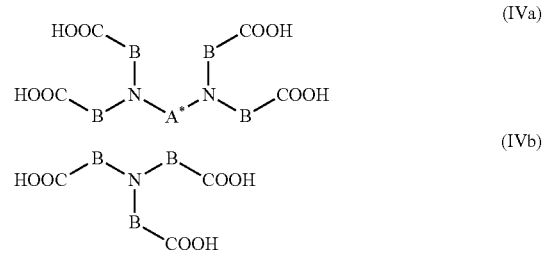

in which the variable A* is a straight-chain or branched $C_2$- to $C_6$-alkylene group or the moiety of the formula V

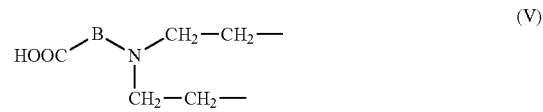

and the variable B is a $C_1$- to $C_{19}$-alkylene group.

Moreover, the preferred oil-soluble reaction product of component (ii), especially that of the general formula IVa or IVb, is an amide, an amide-ammonium salt or an ammonium salt in which no, one or more carboxylic acid groups have been converted to amide groups.

Straight-chain or branched $C_2$- to $C_6$-alkylene groups of the variable A* are, for example, 1,1-ethylene, 1,2-propylene, 1,3-propylene, 1,2-butylene, 1,3-butylene, 1,4-butylene, 2-methyl-1,3-propylene, 1,5-pentylene, 2-methyl-1,4-butylene, 2,2-dimethyl-1,3-propylene, 1,6-hexylene (hexamethylene) and in particular 1,2-ethylene. The variable A* comprises preferably 2 to 4 and especially 2 or 3 carbon atoms.

$C_1$- to $C_{19}$-alkylene groups of the variable B are before, for example, 1,2-ethylene, 1,3-propylene, 1,4-butylene, hexamethylene, octamethylene, decamethylene, dodecamethylene, tetradecamethylene, hexadecamethylene, octadecamethylene, nonadecamethylene and especially methylene. The variable B comprises preferably 1 to 10 and especially 1 to 4 carbon atoms.

The primary and secondary amines as a reaction partner for the polycarboxylic acids to form component (ii) are typically monoamines, especially aliphatic monoamines. These primary and secondary amines may be selected from a multitude of amines which bear hydrocarbyl radicals optionally joined to one another.

These amines underlying the oil-soluble reaction products of component (ii) are preferably secondary amines and have the general formula HN(R*)$_2$ in which the two variables R* are each independently straight-chain or branched $C_{10}$- to $C_{30}$-alkyl radicals, especially $C_{14}$- to $C_{24}$-alkyl radicals. These relatively long-chain alkyl radicals are preferably straight-chain or only slightly branched. In general, the secondary amines mentioned, with regard to their relatively long-chain alkyl radicals, derive from naturally occurring fatty acids or from derivatives thereof. The two R* radicals are preferably identical.

The secondary amines mentioned may be bonded to the polycarboxylic acids by means of amide structures or in the form of the ammonium salts; it is also possible for only a portion to be present as amide structures and another portion as ammonium salts. Preferably only few, if any, free acid groups are present. In a preferred embodiment, the oil-soluble reaction products of component (ii) are present completely in the form of the amide structures.

Typical examples of such components (ii) are reaction products of nitrilotriacetic acid, of ethylenediaminetetraacetic acid or of propylene-1,2-diaminetetraacetic acid with in each case 0.5 to 1.5 mol per carboxyl group, especially 0.8 to 1.2 mol per carboxyl group, of dioleylamine, dipalmitinamine, dicocoamine, distearylamine, dibehenylamine or especially ditallowamine. A particularly preferred component (ii) is the reaction product of 1 mol of ethylenediaminetetraacetic acid and 4 mol of hydrogenated ditallowamine.

Further typical examples of component (ii) include the N,N-dialkylammonium salts of 2-N',N'-dialkylamidobenzoates, for example the reaction product of 1 mol of phthalic anhydride and 2 mol of ditallowamine, the latter being hydrogenated or unhydrogenated, and the reaction product of 1 mol of an alkenylspirobislactone with 2 mol of a dialkylamine, for example ditallowamine and/or tallowamine, the last two being hydrogenated or unhydrogenated.

Further typical examples of component (ii) include monoamides of dicarboxylic acids, which by reaction of dicarboxylic acids or reactive dicarboxylic acid derivatives, such as anhydrides thereof, with primary or secondary amines having straight-chain or branched $C_{10}$ to $C_{30}$ alkyl radicals mentioned, for example the reaction product of 1 mol of maleic anhydride with 1 mol of a long-chain primary amine such as isotridecylamine.

Further typical structure types for the component of class (ii) are cyclic compounds with tertiary amino groups or condensates of long-chain primary or secondary amines with carboxylic acid-containing polymers, as described in WO 93/18115.

For component (ii), it is also possible to use mixtures of various species, for example a mixture of an oil-soluble reaction product based on poly($C_2$- to $C_{20}$-carboxylic acids) which have at least one tertiary amino group and are of the general formula IVa or IVb with a monoamide of a dicarboxylic acid.

For component (iii), it is possible in principle to use any organic compounds which are capable of improving the cold flow characteristics of mineral oils and crude oils. For the intended purpose, they must have sufficient oil solubility. Especially suitable for this purpose are cold flow improvers (MDFIs) typically used in the case of middle distillates of mineral or fossil origin, i.e. in the case of conventional diesel fuels and heating oils. However, it is also possible to use, as component (iii), organic compounds which, when used in conventional diesel fuels and heating oils, partly or predominantly have the properties of a wax antisettling additive (WASA). They also partly or predominantly act as nucleators.

More particularly, component (iii), which generally represents a different substance class than component (ii), is selected from the abovementioned substance classes (a1) to (a6), (a1) being of particular interest.

The inventive mixture can be added directly, i.e. in undiluted form, to the mineral oils and crude oils, especially to the middle distillate fuels, but is preferably added as a 5 to 90% by weight, especially as a 10 to 70% by weight and in particular as a 25 to 60% by weight solution (concentrate) in a suitable solvent, typically a hydrocarbon solvent. Such a concentrate comprising 5 to 90% by weight, especially 10 to 70% by weight and in particular 25 to 60% by weight, based on the total amount of the concentrate, of the inventive mixture dissolved in a hydrocarbon solvent therefore also forms part of the subject matter of the present invention. Common solvents in this context are aliphatic or aromatic hydrocarbons, for example xylenes or mixtures of high-boiling aromatics such as Solvent Naphtha. It is also advantageously possible here to use low-naphthalene aromatic hydrocarbon mixtures such as low-naphthalene Solvent Naphtha as solvents. Additionally suitable for this purpose are also solvents from the group of the alcohols, esters and ethers, including the polyoxyalkylenes and the polyglycols, these being soluble in biofuel oils and middle distillates. It is also possible to use middle distillate fuels themselves as solvents for such concentrates.

The dosage of the mixture in the mineral oils and crude oils, especially in the middle distillate fuels, is generally 10 to 10 000 ppm by weight, especially 50 to 5000 ppm by weight, in particular 100 to 3000 ppm by weight, for example 500 to 1500 ppm by weight, based in each case on the total amount of oil or fuel.

The inventive mixture can be used as an additive to middle distillate fuels which consist
(A) to an extent of 0.1 to 100% by weight, preferably to an extent of 0.1 to less than 100% by weight, especially to an extent of 10 to 95% by weight and in particular to an extent of 30 to 90% by weight, of at least one biofuel oil which is based on fatty acid esters, and
(B) to an extent of 0 to 99.9% by weight, preferably to an extent of more than 0 to 99.9% by weight, especially to an extent of 5 to 90% by weight and in particular to an extent of 10 to 70% by weight, of middle distillates of fossil origin and/or of vegetable and/or animal origin, which are essentially hydrocarbon mixtures and are free of fatty acid esters.

The fuel component (A) is usually also referred to as "biodiesel". The middle distillates of fuel component (A) preferably essentially comprise alkyl esters of fatty acids which derive from vegetable and/or animal oils and/or fats. Alkyl esters are typically understood to mean lower alkyl esters, especially $C_1$- to $C_4$-alkyl esters, which are obtainable by transesterifying the glycerides, especially triglycerides, which occur in vegetable and/or animal oils and/or fats by means of lower alcohols, for example ethanol, n-propanol, isopropanol, n-butanol, isobutanol, sec-butanol, tert-butanol or in particular methanol ("FAME").

Examples of vegetable oils which can be converted to corresponding alkyl esters and can thus serve as the basis for biodiesel are castor oil, olive oil, peanut oil, palm kernel oil, coconut oil, mustard oil, cottonseed oil and especially sunflower oil, palm oil, soybean oil and rapeseed oil. Further examples include oils which can be obtained from wheat, jute, sesame and shea tree nut; it is also possible to use arachis oil, jatropha oil and linseed oil. The extraction of these oils and their conversion to the alkyl esters are known from the prior art or can be derived therefrom.

It is also possible to convert already used vegetable oils, for example used deep fat fryer oil, optionally after appropriate cleaning, to alkyl esters and thus for them to serve as the basis for biodiesel. Vegetable fats can in principle likewise be used as a source for biodiesel, but play a minor role.

Examples of animal fats and oils which are converted to corresponding alkyl esters and can thus serve as the basis for biodiesel are fish oil, bovine tallow, porcine tallow and similar fats and oils obtained as wastes in the slaughter or utilization of farm animals or wild animals.

The parent saturated or unsaturated fatty acids of the vegetable and/or animal oils and/or fats mentioned, which usually have 12 to 22 carbon atoms and may bear additional functional groups such as hydroxyl groups, and which occur in the alkyl esters, are especially lauric acid, myristic acid, palmitic acid, stearic acid, oleic acid, linoleic acid, linolenic acid, elaidic acid, erucic acid and/or ricinoleic acid.

Typical lower alkyl esters based on vegetable and/or animal oils and/or fats, which find use as biodiesel or biodiesel components, are, for example, sunflower methyl ester, palm oil methyl ester ("PME"), soybean oil methyl ester ("SME") and especially rapeseed oil methyl ester ("RME").

However, it is also possible to use the monoglycerides, diglycerides and especially triglycerides themselves, for example castor oil, or mixtures of such glycerides, as biodiesel or components for biodiesel.

In the context of the present invention, the fuel component (B) shall be understood to mean middle distillate fuels boiling in the range from 120 to 450° C. Such middle distillate fuels are used especially as diesel fuel, heating oil or kerosene, particular preference being given to diesel fuel and heating oil.

Middle distillate fuels refer to fuels which are obtained by distilling crude oil as the first process step and boil within the range from 120 to 450° C. Preference is given to using low-sulfur middle distillates, i.e. those which comprise less than 350 ppm of sulfur, especially less than 200 ppm of sulfur, in particular less than 50 ppm of sulfur. In special cases, they comprise less than 10 ppm of sulfur; these middle distillates are also referred to as "sulfur-free". They are generally crude oil distillates which have been subjected to refining under hydrogenating conditions and therefore comprise only small proportions of polyaromatic and polar compounds. They are preferably those middle distillates which have 90% distillation points below 370° C., especially below 360° C. and in special cases below 330° C.

Low-sulfur and sulfur-free middle distillates may also be obtained from relatively heavy mineral oil fractions which cannot be distilled under atmospheric pressure. Typical conversion processes for preparing middle distillates from heavy crude oil fractions include: hydrocracking, thermal cracking, catalytic cracking, coking processes and/or visbreaking. Depending on the process, these middle distillates are obtained in low-sulfur or sulfur-free form, or are subjected to refining under hydrogenating conditions.

The middle distillates preferably have aromatics contents of below 28% by weight, especially below 20% by weight. The content of normal paraffins is between 5% by weight and 50% by weight, preferably between 10 and 35% by weight.

The middle distillates referred to as fuel component (B) shall also be understood here to mean middle distillates which can either be derived indirectly from fossil sources such as mineral oil or natural gas, or else are prepared from biomass via gasification and subsequent hydrogenation. A typical example of a middle distillate fuel which is derived indirectly from fossil sources is the GTL ("gas-to-liquid") diesel fuel obtained by means of Fischer-Tropsch synthesis. A middle distillate is prepared from biomass, for example via the BTL ("biomass-to-liquid") process, and can be used either alone or in a mixture with other middle distillates as fuel component (B). The middle distillates also include hydrocarbons which are obtained by the hydrogenation of fats and fatty oils. They comprise predominantly n-paraffins. It is common to the middle distillate fuels mentioned that they are essentially hydrocarbon mixtures and are free of fatty acid esters.

The qualities of the heating oils and diesel fuels are laid down in more detail, for example, in DIN 51603 and EN 590 (cf. also Ullmann's Encyclopedia of Industrial Chemistry, 5th edition, volume A12, p. 617 ff., which is hereby incorporated explicitly by reference).

The inventive mixture may be added either to pure middle distillate fuels of mineral or fossil origin or to mixtures thereof with biofuel oils (biodiesel) to improve their properties. In both cases, a significant improvement in the cold flow characteristics of the fuel is observed, i.e. a lowering especially of the CFPP values, but also the CP values and/or the PP values, irrespective of the origin or the composition of the fuel. The CFPP values are determined here—and also in relation to the inventive use of the substituted ureas and urethanes (i) for further improvement of the cold flow properties in combination with components (iii) and optionally (ii)—typically to the standard EN 116, and the CP values typically to the standard ISO 3015. The crystals which precipitate out are generally effectively kept suspended, and so there are no blockages of filters and lines by such sediments. The inventive mixture in most cases has a good activity spectrum and thus has the effect that the crystals which precipitate out are dispersed very efficiently in a wide variety of different fuels.

Equally, the use of the inventive mixture can improve a series of further fuel properties. Mention shall be made here by way of example merely of the additional effect as a corrosion protectant or the improvement of the oxidation stability.

The present invention also provides middle distillate fuels, optionally with a content of biofuel oils (biodiesel).

In general, the middle distillate fuels mentioned or the fuel additive concentrates mentioned also comprise, as further additives in amounts customary therefor, conductivity improvers, anticorrosion additives, lubricity additives, antioxidants, metal deactivators, antifoams, demulsifiers, detergents, cetane number improvers, solvents or diluents, dyes or fragrances or mixtures thereof. The further additives which have been mentioned above but have not yet been addressed above, are familiar to those skilled in the art and therefore need not be explained any further here.

The examples which follow are intended to illustrate the present invention without restricting it.

Abbreviations:
Ilco-Min 8015 C $C_{12}$-$C_{14}$ cocoamine technical grade, equivalent weight 208
Ilco-Min 8040 T $C_{16}$-$C_{18}$ tallowamine, partly unsaturated, equivalent weight 271
Inipol DS N-tallowalkyl-1,3-propanediamine, equivalent weight 299
IPDA isophoronediamine
IPDI isophorone diisocyanate
HMDI dicyclohexylmethane 4,4'-diisocyanate
4,4'-MDI diphenylmethane 4,4'-diisocyanate
Solvesso® 150 aromatic solvent, boiling range 181-207° C.

PREPARATION EXAMPLES 1-6

Diureas from Diisocyanate and Monoamine

A stirred flask with thermometer and reflux condenser was initially charged with 160 g of Solvesso® 150 and the isocyanate, and the amine was added by means of a dropping funnel within 15 minutes. The dropping funnel was rinsed with 20 g of Solvesso® 150. After one hour, the reaction had ended.

| Example No. | Isocyanate | Amount (g) | Number of moles (mmol) | Amine | amount (g) | Number of moles (mmol) |
|---|---|---|---|---|---|---|
| 1 | IPDI | 8.9 | 40 | 2-Ethylhexylamine | 10.37 | 80 |
| 2 | IPDI | 8.9 | 40 | n-Dodecylamine | 14.87 | 80 |
| 3 | IPDI | 8.9 | 40 | Ilco-Min 8040 T | 21.75 | 80 |
| 4 | IPDI | 8.9 | 40 | Ilco-Min 8015 C | 16.70 | 80 |
| 5 | HMDI | 10.5 | 40 | Isotridecylamine | 16.0 | 80 |
| 6 | 4,4'-MDI | 10.0 | 40 | Isotridecylamine | 16.0 | 80 |

PREPARATION EXAMPLES 7-12

Polyureas from Diisocyanate, Monoamine and Diamine

A stirred flask with thermometer and reflux condenser was initially charged with 160 g of Solvesso® 150 and the amines, and the isocyanate was added by means of a dropping funnel within 15 minutes. The dropping funnel was rinsed with 20 g of Solvesso® 150. After one hour, the reaction had ended.

| Example No. | Iso-cyanate | Amount (g) | Number of moles (mmol) | Monoamine Diamine | Amount (g) | Number of moles (mmol) |
|---|---|---|---|---|---|---|
| 7 | IPDI | 8.9 | 40 | Isotridecylamine | 8.0 | 40 |
|   |   |   |   | IPDA | 3.4 | 20 |
| 8 | IPDI | 13.3 | 60 | Isotridecylamine | 8.0 | 40 |
|   |   |   |   | IPDA | 6.8 | 40 |
| 9 | IPDI | 8.9 | 40 | Isotridecylamine | 4.0 | 20 |
|   |   |   |   | IPDA | 5.1 | 30 |
| 10 | IPDI | 8.9 | 40 | Isotridecylamine | 8.0 | 40 |
|   |   |   |   | Inipol DS | 6.0 | 20 |
| 11 | IPDI | 6.7 | 30 | Isotridecylamine | 4.0 | 20 |
|   |   |   |   | Inipol DS | 6.0 | 20 |
| 12 | IPDI | 8.9 | 40 | Isotridecylamine | 4.0 | 20 |
|   |   |   |   | Inipol DS | 9.0 | 30 |

PREPARATION EXAMPLES 13 AND 14

Diurethanes from Diisocyanate and Monool

A stirred flask with thermometer and reflux condenser was initially charged with 160 g of Solvesso® 150 and the alcohol, and the isocyanate was added by means of a dropping funnel within 15 minutes. The dropping funnel was rinsed with 20 g of Solvesso® 150. After 24 hours, the reaction had ended.

| Example No. | Iso-cyanate | Amount (g) | Number of moles (mmol) | Monool | Amount (g) | Number of moles (mmol) |
|---|---|---|---|---|---|---|
| 13 | IPDI | 8.9 | 40 | Isotridecanol | 16.1 | 80 |
| 14 | IPDI | 8.9 | 40 | n-Tridecanol | 16.1 | 80 |

USE EXAMPLES 1 TO 3

Diesel fuel DF1 of the specification specified below was admixed with 300 ppm by weight of a 60% by weight solution of a commercial ethylene-vinyl acetate copolymer with a vinyl acetate content of 30% by weight in Solvent® Naphtha as a cold flow improver ("CI") and with 300 ppm by weight of a solution of two wax antisettling additives ("WASAs") and of a substituted urea of the general formula (I) in Solvent® Naphtha ("FI"), mixed at 40° C. by stirring and then cooled to room temperature. The CP of this additized fuel sample was determined to ISO 3015 and the CFPP to EN 116. Thereafter, the additized fuel sample was cooled to −15° C. in a 250 ml glass cylinder in a cold bath at −25° C. within 3 hours, and stirred at this temperature for 13 hours. For each sample, the CP was again determined on the 20% by volume base phase separated off at −15° C. to ISO 3015, and the CFPP to EN 116.

Specification of the diesel fuel DF1:

| | | |
|---|---|---|
| Cloud Point (CP): | | −7.9° C. |
| Cold Filter Plugging Point (CFPP): | | −9° C. |
| Pour Point (PP): | | −12° C. |
| Density (15° C.): | | 826.6 kg/m³ |
| Boiling points: | IBP | 181° C. |
| | 10% | 220° C. |
| | 20% | 234° C. |
| | 50% | 268° C. |
| | 90% | 327° C. |
| | 95% | 341° C. |
| | FBP | 350° C. |
| WASA additives: | K1 = ethylenediaminetetraacetic acid reacted with 4 mol of hydrogenated tallowamine | |
| | K2 = maleic anhydride reacted with 1 mol of isotridecylamine | |

Composition of the FI solutions:

FI1: 35 parts by weight of K1
    10 parts by weight of K2
    15 parts by weight of diurea from 1 mol of isophorone diisocyanate and 2 mol of isotridecylamine [compound of the formula (IIg)]
    40 parts by weight of Solvent ® Naphtha
FI2: 35 parts by weight of K1
    10 parts by weight of K2
    55 parts by weight of Solvent ® Naphtha The following table shows the results of the CP and CFPP measurements [in each case in ° C.], experiment 2 with FI2 serving as a comparison:

| Experiment | FI | CP | CP(up) | ΔCP | CFPP | CFPP(up) | ΔCFPP |
|---|---|---|---|---|---|---|---|
| 1 | FI1 | −7.6 | −6.7 | 0.9 | −27 | −26 | 1 |
| 3 | FI3 | −7.9 | −5.1 | 2.8 | −21 | −20 | 1 |

The smaller the deviation ("ΔCP") in the CP of the 20% by volume base phase ["CP(up)"] from the original CP of the respective fuel sample, the better the dispersion of the paraffins. The smaller the deviation ("ΔCFPP") in the CFPP of the 20% by volume base phase ["CFPP(up)"] from the original CFPP of the respective fuel sample, the better the cold flow characteristics.

The invention claimed is:

1. A method for improving use properties of a mineral or synthetic nonaqueous industrial fluid, comprising:
combining the mineral or synthetic nonaqueous industrial fluid with a substituted urea or urethane of general formula (I):

$$R^1X\text{—}CO\text{—}NR^3R^4 \qquad (I)$$

where:
X is $R^2N$;
each of $R^1$ and $R^3$ is hydrogen;
$R^4$ is a $C_4$- to $C_{30}$-alkyl radical which may be interrupted by one or more oxygen atoms, a $C_4$- to $C_{30}$-alkenyl radical, a $C_5$- to $C_{30}$-cycloalkyl radical, a $C_6$- to $C_{30}$-aryl radical, or a $C_7$- to $C_{30}$-arylalkyl radical; and
$R^2$ is a radical of formula (Ia):

$$\text{-A-}(X'\text{—}CO\text{-A'})_n\text{-}X'\text{—}CO\text{—}NR^6R^7 \qquad (Ia)$$

where:
A and each A' are independently an aliphatic, cycloaliphatic, aromatic, or aliphatic-aromatic bridging element having 1 to 20 carbon atoms;
X' is $NR^5$ or O;
n is an integer from 0 to 50;
each of $R^5$ and $R^7$ is hydrogen; and
$R^6$ is the same as $R^4$.

2. The method of claim 1, wherein A is 3,5,5-trimethylcyclohexan-1-ylene-3-methylene, 1,6-hexamethylene, 2,4-tolylene, 2,6-tolylene, dicyclohexylmethan-4,4'-ylene, or diphenylmethan-4,4'-ylene.

3. The method of claim 1, comprising combining a mineral oil or crude oil with the substituted urea or urethane of general formula (I).

4. The method of claim 1, comprising combining a fuel with the substituted urea or urethane of general formula (I).

5. The method of claim 4, wherein the fuel is a fuel from which paraffin crystals have precipitated out.

6. The method of claim 4, comprising combining the fuel, the substituted urea or urethane of general formula (I), and at least one organic compound selected from the group consisting of a copolymer of a $C_2$- to $C_{40}$-olefin with at least one further ethylenically unsaturated monomer, a comb polymer, a polyoxyalkylene, a polar nitrogen compound, a sulfocarboxylic acid, a sulfocarboxylic acid derivative, a sulfonic acid, a sulfonic acid derivative, and a poly(meth) acrylic ester.

7. The method of claim 1, comprising combining a mineral or synthetic lubricant with the substituted urea or urethane of general formula (I).

8. A lubricant formulation obtained by the method of claim 7.

9. A mixture, comprising:
(i) 1 to 99% by weight of a substituted urea or substituted urethane of formula (I):

$$R^1X\text{—}CO\text{—}NR^3R^4 \qquad (I)$$

where:
X is $R^2N$;
each of $R^1$ and $R^3$ is hydrogen;
$R^4$ is a $C_4$- to $C_{30}$-alkyl radical which may be interrupted by one or more oxygen atoms, a $C_4$- to $C_{30}$-alkenyl radical, a $C_5$- to $C_{30}$-cycloalkyl radical, a $C_6$- to $C_{30}$-aryl radical, or a to $C_7$-$C_{30}$-arylalkyl radical; and
$R^2$ is a radical of formula (Ia):

$$\text{-A-}(X'\text{—}CO\text{-A'})_n\text{—}X'\text{—}CO\text{—}NR^6R^7 \qquad (Ia)$$

where:
A and each A' are independently an aliphatic, cycloaliphatic, aromatic, or aliphatic-aromatic bridging element having 1 to 20 carbon atoms;
X' is $NR^5$ or O;
n is an integer from 0 to 50;
each of $R^5$ and $R^7$ is hydrogen; and
$R^6$ is the same as $R^4$;
(ii) 0 to 50% by weight of an organic compound suitable for dispersion or for promoting dispersion of paraffin crystals which precipitate out of mineral oils or crude oils under cold conditions; and
(iii) 1 to 99% by weight of an organic compound which improves cold flow characteristics of a mineral oil or a crude oil;
wherein components (i) to (iii) sum to 100% by weight.

10. A method, comprising combining the mixture of claim 9 and a fuel.

11. A fuel, comprising the mixture of claim 9.

12. The fuel of claim 11, further comprising at least one additive selected from the group consisting of a flow improver, a paraffin dispersant, a conductivity improver, an anticorrosion additive, a lubricity additive, an antioxidant, a metal deactivator, an antifoam, a demulsifier, a detergent, a cetane number improver, a solvent, a diluent, a dye, and a fragrance.

13. A fuel additive concentrate, comprising the mixture of claim 9 dissolved in a hydrocarbon solvent, wherein:
the mixture is present in an amount of 10 to 70% by weight based on a total weight of the concentrate.

14. The fuel additive concentrate of claim 13, further comprising an additive selected from the group consisting of a flow improver, a paraffin dispersant, a conductivity improver, an anticorrosion additive, a lubricity additive, an antioxidant, a metal deactivator, an antifoam, a demulsifier, a detergent, a cetane number improver, a solvent, a diluent, a dye, and a fragrance.

15. The method of claim 4, wherein the fuel is a middle distillate fuel.

16. The lubricant formulation of claim 8, further comprising a lubricant additive.

17. The method of claim 10, wherein the fuel is a middle distillate fuel.

18. A middle distillate fuel, comprising the mixture of claim 9.

* * * * *